United States Patent [19]

Willis et al.

[11] Patent Number: 4,759,359
[45] Date of Patent: Jul. 26, 1988

[54] LENS IMPLANTATION INSTRUMENT

[75] Inventors: Timothy R. Willis; Lyle E. Paul, both of El Toro; Stanley L. Van Gent, Laguna Beach, all of Calif.

[73] Assignee: Allergan, Inc., Irvine, Calif.

[21] Appl. No.: 91,203

[22] Filed: Aug. 31, 1987

[51] Int. Cl.⁴ ............................................. A61B 17/36
[52] U.S. Cl. ..................................... 128/303 R; 623/6
[58] Field of Search .............. 128/303 R, 321; 623/4, 623/6; 604/51; 351/205, 211, 213, 214

[56] References Cited

U.S. PATENT DOCUMENTS

| | | | |
|---|---|---|---|
| 4,190,049 | 2/1980 | Hager et al. | 128/303 R |
| 4,198,980 | 4/1980 | Clark | 128/303 R |
| 4,214,585 | 7/1980 | Bailey, Jr. | 128/303 R |
| 4,530,117 | 7/1985 | Kelman | 128/303 R |
| 4,643,185 | 2/1987 | Gaba | 128/303 R |
| 4,657,011 | 4/1987 | Gaba | 128/303 R |
| 4,676,792 | 1/1987 | Praeger | 128/303 R |
| 4,699,140 | 10/1987 | Holmes et al. | 128/303 R |
| 4,702,244 | 10/1987 | Mazzocco | 128/303 R |
| 4,706,666 | 11/1987 | Sheets | 128/303 R |
| 4,715,373 | 12/1987 | Mazzocco et al. | 128/303 R |

OTHER PUBLICATIONS

Product description for a Model E2999-M Mazzacco Lens Forceps marketed by Storz Instrument Company of St. Louis, MO (one page with picture).

Primary Examiner—Raymond A. Nelli
Attorney, Agent, or Firm—Loyal M. Hanson

[57] ABSTRACT

A lens implantation instrument includes first and second prongs connected together in a forceps-like configuration that is adapted to be grasped in the hand of a user for purposes of holding an intraocular lens to be implanted in an eye. The first prong has a distal end portion that defines a trough extending distally, the trough having a size and shape adapted to receive at least a portion of the optic of the lens with the optic in a folded configuration, and the second prong has a distal end portion that extends generally parallel to the trough, the distal end portion of the second prong having a size and shape adapted to fit at least partially into the trough. The first and second prongs are connected to enable the user to move the distal end portions relative to one another between an opened position in which the distal end portions are spaced apart sufficiently to enable placement of the lens between the distal end portions and a closed position in which the distal end portion of the second prong retains at least a portion of the lens in the trough with the lens in a folded configuration. The first and second prongs are also connected to enable the user to retract the distal end portion of the second prong proximally relative to the trough in order to facilitate release of the lens.

9 Claims, 2 Drawing Sheets

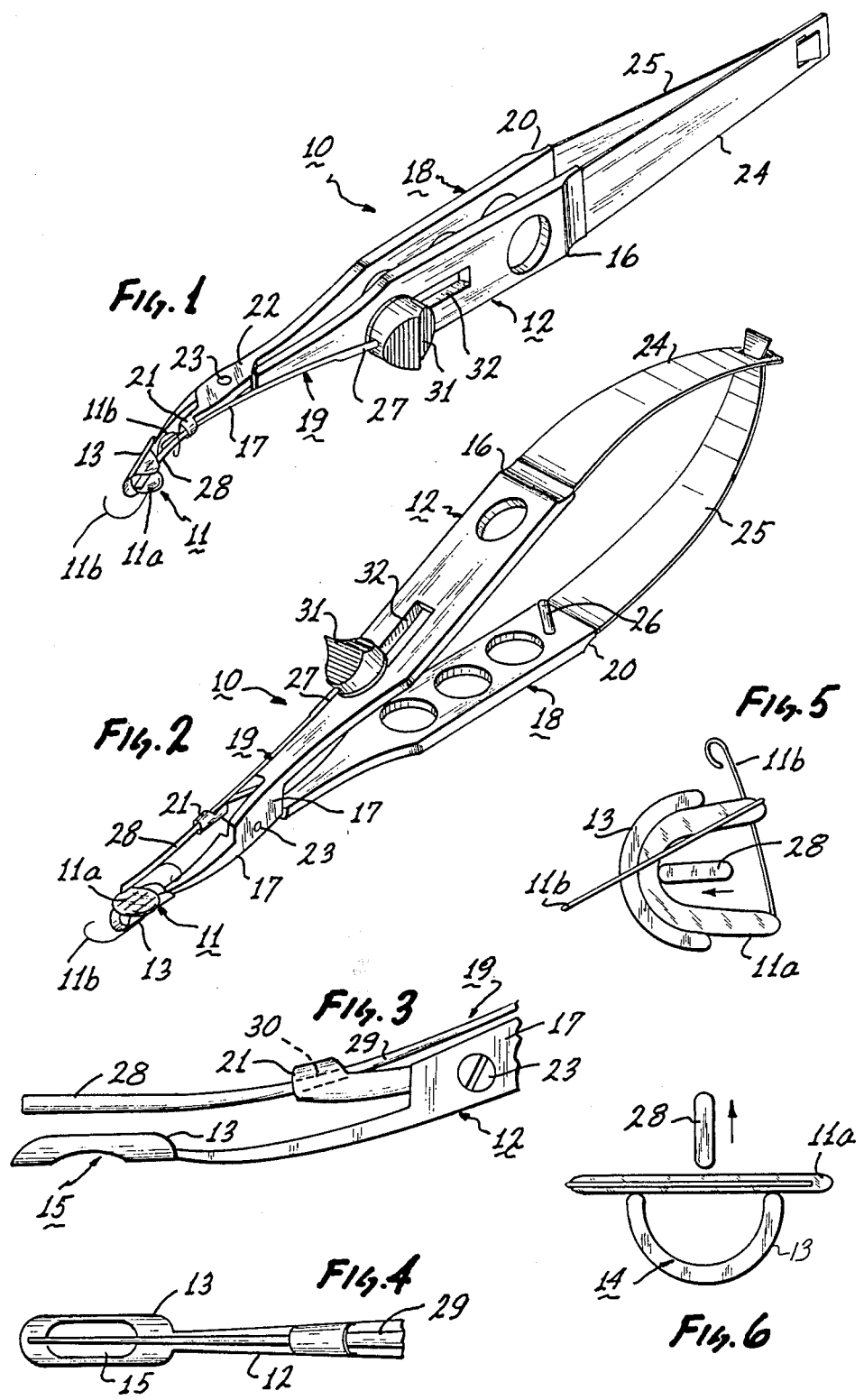

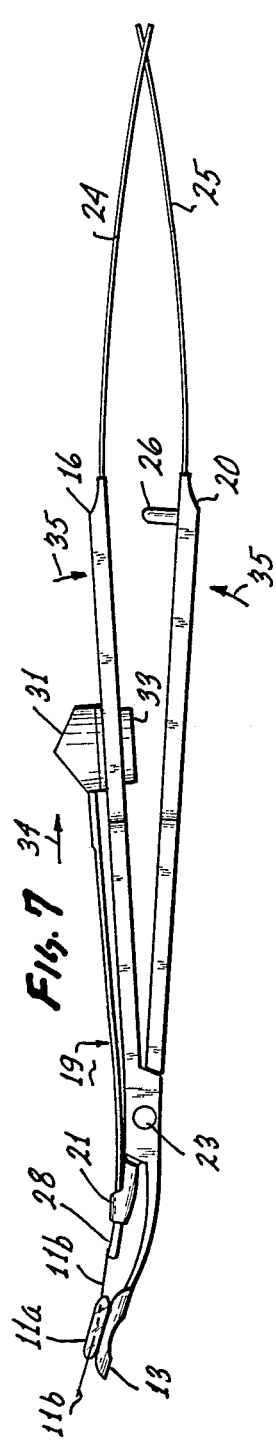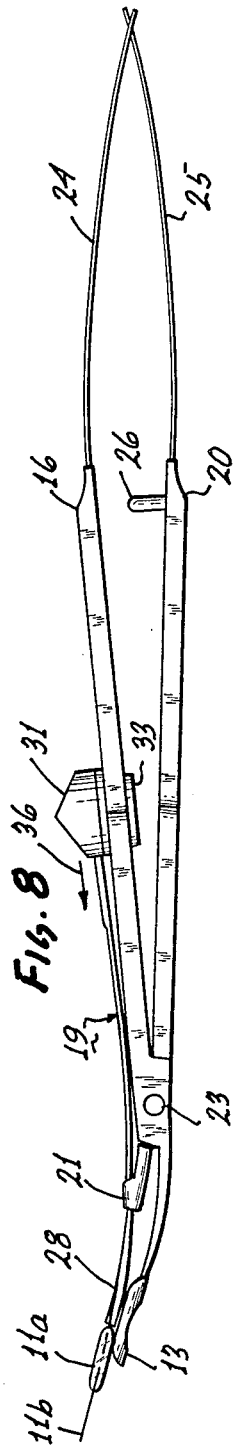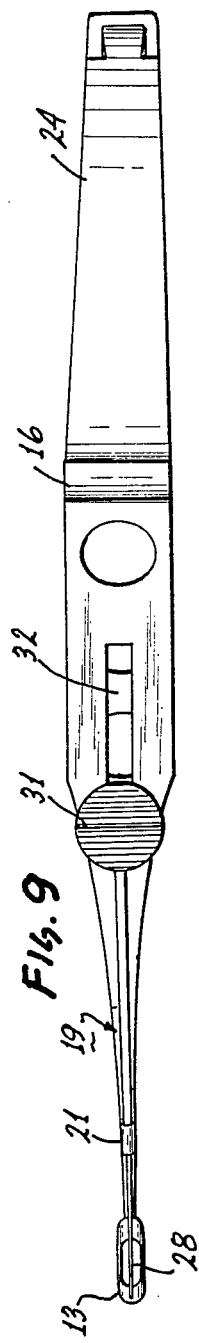

LENS IMPLANTATION INSTRUMENT

BACKGROUND OF THE INVENTION

1. Technical Field

This invention relates generally to surgical instruments, and more particularly to a new and improved instrument for implanting an intraocular lens.

2. Backqround Information

The optic or optic portion of an intraocular lens may be on the order of six to seven millimeters in diameter, and implantation within an eye involves very delicate and precise manipulation of the lens through an incision in the eye. In the case of a soft or foldable intraocular lens, the surgeon folds the lens so that it will fit through a smaller, three to three and one-half millimeter incision. Then, the surgeon passes the lens through the incision, allows the lens to unfold within the eye, and manipulates it into a desired position.

This is done sometimes with a handheld forceps-like instrument having opposing jaws between which the lens is held. With the lens held in a folded configuration between the jaws, the surgeon passes the lens through the incision into the eye interior. Next, the surgeon separates the jaws to release the lens, and then retracts the jaws back out of the incision.

However, certain problems accompany this procedure. For example, the instrument may be awkward to use once the jaws are within the eye. In other words, the jaws may be restricted by the small incision, thereby complicating movement to an opened position and manipulation to release the lens. Consequently, it is desirable to have an instrument better adapted to operation in this restricted position.

In addition, the jaws of existing instruments may be difficult to withdraw through the small incision once they are in the opened position. They may diverge so that the the tips of the jaws are separated by a distance greater than the opening provided by the incision. The surgeon must somehow dislodge the lens from the jaws so that the jaws can be closed prior to withdrawal, and this procedure may be somewhat uncertain. Consequently, it is desirable to have an instrument that alleviates this concern.

Moreover, the jaws of existing instruments may damage the optic portion of a soft intraocular lens. This is generally the central portion of the lens, and pinching it between the jaws may degrade its optical characteristics. Consequently, it is desirable to have an instrument designed to alleviate this concern also.

SUMMARY OF THE INVENTION

This invention recognizes the problems associated with the prior art and provides a new and improved lens implantation instrument with the desired attributes.

Briefly, the above and further objects of the present invention are realized by providing an instrument having a trough-shaped jaw in which to hold the lens in a folded configuration with a pivotally operated opposing jaw in the form of an elongated element. The elongated element can be retracted proximally relative to the trough to facilitate release of the lens within the eye as well as withdrawal of the jaws from the eye. In addition, the trough includes an open base region in the area of the optic that inhibits damage to the lens.

Thus, the instrument is better adapted to operation through a small incision in the eye. Furthermore, it is configured to facilitate withdrawal from the eye, and it features a trough-shaped jaw that is less likely to cause damage to the optic portion of the intraocular lens.

Generally, an instrument constructed according to the invention includes first and second prongs connected together in a forceps-like configuration that is adapted to be grasped in the hand of a user for purposes of holding an intraocular lens to be implanted in an eye. The first prong has a distal end portion that defines a trough extending distally, and the trough has a size and shape adapted to receive at least a portion of the lens with the lens in a folded configuration.

The second prong has a distal end portion that extends generally parallel to the trough, and the distal end portion of the second prong has a size and shape adapted to fit at least partially into the trough. Thus, the distal end portions of the first and second prongs cooperate as jaws between which to retain the lens in a folded configuration.

The first and second prongs are connected together in an arrangement for enabling the user to move the distal end portions relative to one another between opened and closed positions. In the opened position, the distal end portions are spaced apart sufficiently to enable placement of the lens between the distal end portions. In the closed position, the distal end portion of the second prong retains at least a portion of the lens in the trough with the lens in a folded configuration.

According to one aspect of the invention, the second prong is mounted to enable the user to retract the distal end portion of the second prong proximally relative to the trough in order to facilitate release of the lens. For this purpose, the second prong may take the form of an elongated element that is mounted so that it can be moved axially relative to the trough. First, the elongated element is retracted to release the lens. Next, and if desired, it is moved toward the trough to dislodge the lens, and then the jaws are move to the closed position so that the jaws can be withdrawn through the incision.

According to another aspect of the invention, the distal end portion of the first prong defines an open base region of the trough that serves to inhibit damage to the optic portion of the intraocular lens when the lens is retained in the trough.

The above mentioned and other objects and features of this invention and the manner of attaining them will become apparent, and the invention itself will be best understood, by reference to the following description taken in conjunction with the accompanying illustrative drawings.

BRIEF DESCRIPTION OF THE DRAWINGS

FIG. 1 of the drawings is a perspective view of an instrument constructed according to the invention, with a conventional intraocular lens retained in a folded configuration in the trough;

FIG. 2 is another perspective view of the instrument, shown rotated ninety degrees and with the lens released;

FIG. 3 is an enlarged elevational view of the distal end portion of the instrument, shown without the lens;

FIG. 4 is an enlarged top view of the distal end portion, also without the lens;

FIG. 5 is an enlarged end view of the instrument in the position of FIG. 1 illustrating retention of the lens within the trough;

FIG. 6 is an enlarged end view of the instrument in the position of FIG. 2 illustrating release of the lens; and FIGS. 7-9 show operation of the retractable element to disengage the lens from the instrument.

DESCRIPTION OF THE PREFERRED EMBODIMENTS

Referring now to FIGS. 1-2, there is shown a lens implantation instrument 10 constructed according to the invention that is retaining a conventional intraocular lens 11. The lens 11 includes an optic 11a that is on the order of six to seven millimeters in diameter. It is composed of a soft, resiliently deformable material that can be folded for lens implantation purposes, and a pair of fixation members 11b, which in this embodiment are resiliently deformable filaments, are affixed to the optic 11a. The instrument 10 is used to hold the lens 11 in the folded configuration illustrated, and this enables the surgeon to insert it through a smaller incision in the eye than otherwise required.

Generally, the instrument 10 includes first and second prongs connected together in a forceps-like configuration that is adapted to be grasped in the hand of a user for purposes of holding the lens 11. It is forceps-like in the sense that it can be manipulated with one hand to hold the lens between distal end portions of the prongs, and it may be composed of a suitable material such as stainless steel. As an idea of size, the illustrated instrument 10 is approximately twelve centimeters long. Of course, this dimension can be varied to achieve a size that best suits the surgeon.

The first prong is in the form of a first forceps member or first elongated member 12 having a distal end portion 13 that defines a concave channel or trough 14 (FIGS. 5 and 6). The trough 14 extends distally and has a size and shape adapted to receive at least a portion of the lens 11 with the optic 11a in the folded configuration. The trough 14 of the illustrated embodiment extends approximately eight millimeters for this purpose (slightly greater than the diameter of the lens), and it has a generally U-shaped cross section that is slightly less than two millimeters across and one millimeter deep. Although they may be varied, these dimensions are sufficient to enable the trough 14 to receive the lens 11 in the folded configuration illustrated without the lens 11 being creased or otherwise damage.

To further inhibit damage to the lens 11, the distal end portion 13 includes an opening that provides an opened base region 15 of the trough 14 (FIGS. 3 and 4). This serves to inhibit contact with, and therefore damage to, the optic 11a of the intraocular lens 11 when the lens is retained in the trough 14. The opened base region 15 extends distally about five millimeters for this purpose.

In addition, the first elongated member 12 includes a handle portion 16 that the surgeon grasps, and an intermediate portion 17 extending between the handle portion 16 and the distal end portion 13 that is pivotally connected to the second prong as subsequently described.

The second prong includes a second forceps member or second elongated member 18 and a lens folding pin or elongated element 19 which is connected to the first elongated member 12. The second elongated member 18 includes a handle end portion 20, and distal end portion 21, and an intermediate portion 22 extending between the handle end portion 20 and the distal end portion 21. The intermediate portion 22 is pivotally connected to the intermediate portion 17 of the first elongated member by suitable means, such as a screw 23.

This results in a pliers-like pivotal action whereby the surgeon can move the distal end portions 13 and 21 of the first and second elongated members 12 and 18 toward each other by squeezing the handle end portions 16 and 20 toward each other. Leaf spring portions 24 and 25 of the handle portions 16 and 20 augment this action by spring biasing the handle end portions 16 and 20 away from each other. The leaf spring portions 24 and 25 are formed so that they normally curve slightly, as illustrated in FIG. 2, and yet respond to the surgeon's squeeze to deform to the configuration illustrated in FIG. 1. A stop member 26 attached to the second elongated member 18 (FIG. 2) serves to limit pivotal movement so that the handle end portions 16 and 20 do not fully come together when squeezed.

The second elongated member 18 has a size and shape such that the distal end portion 21 is located proximally of the distal end portion 13, and therefore the trough 14. In this position, the distal end portion 13 serves to couple pivotal motion to the elongated element 19. The elongated element 19 includes a proximal end portion 27 connected to the first elongated member 12 (FIGS. 1 and 2), a distal end portion 28 disposed along and generally parallel to the trough 14 (FIG. 3), and an intermediate portion 29 that extends between the proximal end portion 27 and the distal end portion 28 (FIG. 3).

The coupling is accomplished between the distal end portion 21 of the second elongated member 18 and the intermediate portion 29 of the elongated element 19. The distal end portion 21 defines a bore or guideway 30 through which the intermediate portion 29 extends moveably (FIG. 3). When the distal end portion 21 moves, it causes the elongated element 19 to move. Thus, this arrangement serves as means for connecting the elongated element 19 to the second elongated member 18 for pivotal movement of the elongated element 19 with the second elongated member 18 such that the jaws or distal end portions 13 and 28 can move toward and away from each other. Thus, the lens 11 can be gripped by the jaws.

When the handle end portions 16 and 20 are squeezed toward each other, the distal end portion 21 causes the distal end portion 28 of the elongated element 19 (the distal end portion of the second prong) to move toward the trough 14. Thus, this arrangement serves as first means for enabling the surgeon to move the distal end portions 13 and 28 relative to one another between opened and closed positions. In other words, it serves to move the distal end portions 13 and 28 like the jaws of a needle nose pliers and, therefore, the distal end portions 13 and 28 are referred to in some of the claims as jaws.

In the opened position, the distal end portions 13 and 28 are spaced apart sufficiently to enable placement of the lens 11 between them, as illustrated in FIG. 6. Depending on the optical characteristics of the lens, it may be on the order of one millimeter thick so that a separation of the distal end portions 13 and 28 in the opened position on the order of two millimeters is sufficient for this purpose. In the closed position, the distal end portions 13 and 28 are closer together so that the distal end portion 28 retains at least a portion of the lens 11 in the trough 14, with the lens 11 in a folded configuration as illustrated in FIG. 5.

The distal end portions 13 and 28 extend approximately twenty-five millimeters beyond the pivotal connection provided by the screw 23. Thus, the bulkier structure in the vicinity of the screw 23 and that of the distal end portion 21 are sufficiently set back from the distal end portions 13 and 28 to facilitate insertion of just the distal end portions 13 and 28 into the eye. The bulkier structure remains outside the eye.

In addition, the proximal end portion 27 of the elongated element 19 is connected to the first elongated member 12, as subsequently described, at a point set back proximally from the screw 23. This results in the jaws subtending a smaller arc between the opened and closed positions than would occur with the elongated element connected closer to the screw 23. Consequently, the distal end portions 13 and 28 diverge less in the opened position so that they do not complicate manipulation within the eye.

According to another aspect of the invention, the proximal end portion 27 of the elongated element 19 is moveably connected to the first elongated member 12 by suitable means, such as a knurled thumb retractor 31 (FIGS. 1 and 2) so that the elongated element 19 can be retracted proximally relative to the trough 14. Taken in conjunction with the manner in which the elongated element 19 extends moveably through the guideway 30, this arrangement serves as second means for enabling the surgeon to retract the distal end portion 28 of the second prong proximally relative to the trough 14 in order to facilitate disengagement or release of the lens 11. In other words, it serves as means for mounting the elongated element 19 on the first elongated member 12 for movement axially through the guideway 30 to enable retraction of the distal end portion 28 of the elongated element 19 proximally relative to the trough 14. This facilitates release of the lens.

Retraction is accomplished with the illustrated instrument 10 by moving the thumb retractor 31 along a slot 32 in the first elongated member 12 in which the thumb retractor 31 is moveably mounted by suitable known means, such as a nut 33 (FIGS. 7 and 8) on a screw shank portion of the thumb retractor 31 that is not visible in the drawings.

Operationally, the surgeon grasps the instrument 10 by the hand end portions 16 and 20, allowing the distal end portions 13 and 28 to remain in the opened position illustrated in FIG. 3. Then, the lens 11 is placed between the distal end portions 13 and 28 and the handle end portions 16 and 20 are squeezed to retain the lens 11 in a folded configuration as depicted in FIG. 1. This is done so that the fixation members 11b extend axially, the fixation member located proximally being position atop the distal end portion 28 (as opposed to being between the distal end portions 13 and 28).

With the lens 11 held in this manner, the surgeon inserts the lens 11 through an incision in the eye. Normally, this is done so that the distal end portions 13 and 28 are fully within the eye, and the distal end portion 21 is outside the eye. Next, the surgeon slowly allows the distal end portions 13 and 28 to move toward the opened position. This results in the lens 11 unfolding so that it lies atop the distal end portion 13 as illustrated in FIG. 2. Preferably, the surgeon simultaneously rotates the instrument 10 ninety degrees while the lens 11 is unfolding to produce a gentle, controlled unfolding of the lens 11, rather than an abrupt unfolding that may cause the lens 11 to spring off of the distal end portion 13. Rotation also serves to keep the fixation members 11a in a preferred orientation.

Once the foregoing has been accomplished, the surgeon retracts the elongated element 1 by moving the thumb retractor 31 in the direction indicated by an arrow 34 in FIG. 7. This retracts the distal end portion 28 from the lens 11. Next, the surgeon squeezes the handle end portions 16 and 20 so that they move together slightly as indicated by the arrows 35 in FIG. 1.

The instrument 10 may be withdrawn in this position. However, surgeon may instead dislodge the lens by moving the thumb retractor 31 in the direction of an arrow 36 in FIG. 8. This causes the distal end portion 28 to push the lens 11 off of the distal end portion 13 to dislodge the lens 11 from the instrument 10. Then, the instrument 10 is squeezed to the closed position illustrated in FIG. 9, and it is fully withdrawn from the eye.

Thus, the invention provides a new and improved lens implantation instrument. It is better adapted to operation through a small incision in the eye. It facilitates release of the lens. It can be more easily withdrawn from from the eye, and it features a trough-shaped jaw that is less likely to cause damage to the lens optic.

Although an exemplary embodiment of the invention has been shown and described, many changes, modifications, and substitutions may be made by one having ordinary skill in the art without necessarily departing from the spirit and scope of this invention.

What is claimed is:

1. A lens implantation instrument, comprising:
   first and second prongs connected together in a forceps-like configuration that is adapted to be grasped in the hand of a user for purposes of holding an intraocular lens to be implanted in an eye;
   the first prong having a distal end portion that defines a trough extending distally, the trough having a size and shape adapted to receive at least a portion of an optic portion of the lens with the optic portion in a folded configuration;
   the second prong having a distal end portion that extends generally parallel to the trough, the distal end portion of the second prong having a size and shape adapted to fit at least partially into the trough;
   first means for enabling the user to move the distal end portions relative to one another between an opened position in which the distal end portions are spaced apart sufficiently to enable placement of the lens between the distal end portions and a closed position in which the distal end portion of the second prong retains at least a portion of the lens in the trough with the lens in a folded configuration; and
   second means for enabling the user to retract the distal end portion of the second prong proximally relative to the trough in order to facilitate release of the lens.

2. An instrument as recited in claim 1, further comprising:
   means for spring biasing the prongs toward the opened position.

3. An instrument as recited in claim 1, wherein:
   the distal end portion of the first prong defines an open base region of the trough to inhibit damage to the optic portion of the lens when the optic portion is retained in the trough.

4. An instrument as recited in claim 1, wherein:
   the first prong includes a first elongated member;

the second prong includes a second elongated member and an elongated element that includes the distal end portion of the second prong;

the second means includes means for mounting the elongated element for movement proximally relative to the trough; and the first means includes means for connecting the first and second elongated members pivotally to enable movement between the opened and the closed positions.

5. A lens implantation instrument, comprising:

a first elongated member having a handle end portion, a distal end portion, and an intermediate portion extending between the handle end portion and the distal end portion, the distal end portion of the first elongated member defining a trough that extends distally along a trough axis and has a size and shape adapted to receive an optic portion of the lens in a folded configuration;

a second elongated member having a handle end portion, a distal end portion and an intermediate portion extending between the handle end portion and the distal end portion, the distal end portion of the second elongated member defining a guideway that is located proximally of the trough;

an elongated element having a proximal end portion, a distal end portion, and an intermediate portion extending through the guideway between the proximal end portion and the distal end portion, the distal end portion of the elongated element extending along the trough generally parallel to the trough axis and having a size and shape adapted to fit at least partially into the trough;

means for pivotally coupling the intermediate portions of the first and second elongated members to enable the user to manipulate the handle end portions and thereby move the distal end portions of the first elongated member and the elongated element between an opened position in which the distal end portions of the first elongated member and the elongated element are spaced apart sufficiently to enable placement of the lens between the distal end portions of the first elongated member and the elongated element, and a closed position in which the distal end portion of the elongated element retains at least a portion of the optic portion of the lens in the trough in a folded configuration; and means for mounting the elongated element on the first elongated member for movement axially through the guideway to enable retraction of the distal end portion of the elongated element proximally relative to the trough in order to facilitate release of the lens.

6. An instrument as recited in claim 5, further comprising:

means for spring biasing the elongated members toward the opened position.

7. An instrument as recited in claim 5, wherein the means for mounting the elongated element includes:

means for moveably connecting the proximal end portion of the elongated element to the handle end portion of the first elongated member so that the elongated element can be manually retracted proximally relative to the trough through the guideway.

8. An instrument as recited in claim 5, wherein:

the distal end portion of the first elongated member defines an open base region of the trough to inhibit damage to an optic portion of the lens when the lens is retained the trough.

9. A lens implantation instrument, comprising:

first and second elongated members;

means for pivotally connecting said first and second members in a configuration that is adapted to be grasped in the hand of a user for purposes of holding an intraocular lens to be implanted in an eye;

the first elongated member having a distal end portion and a concave jaw at the distal end portion which has a size and shape adapted to at least partially receive an optic portion of the lens in a folded configuration;

an elongated element having a distal end portion and a jaw at the distal end portion of the elongated element having a size and shape adapted to cooperate with the jaw of the first elongated member;

means for connecting the elongated element to the second elongated member for pivotal movement of the elongated element with the second elongated member such that the jaws can move toward and away from each other whereby the lens can be gripped by the jaws; and means for mounting the elongated element on the first elongated member for movement of the elongated element proximally relative to the jaw of the first elongated member in order to facilitate release of the lens from the jaws.

* * * * *